United States Patent [19]

Benner

[11] Patent Number: 4,638,032

[45] Date of Patent: Jan. 20, 1987

[54] MAGNETIC PARTICLES AS SUPPORTS FOR ORGANIC SYNTHESIS

[75] Inventor: Steven A. Benner, Cambridge, Mass.

[73] Assignee: Genetics Institute, Inc., Cambridge, Mass.

[21] Appl. No.: 640,027

[22] Filed: Aug. 10, 1984

[30] Foreign Application Priority Data

Dec. 12, 1983 [CA] Canada ................................... 443105
Dec. 12, 1983 [EP] European Pat. Off. ........ 82103253.7

[51] Int. Cl.$^4$ ...................... C08F 283/12; H01F 1/00; C09D 5/23
[52] U.S. Cl. ................................ 525/54.11; 525/54.1; 536/27; 536/28; 536/29; 536/18.5; 536/124; 252/62.51
[58] Field of Search .................... 536/27, 28, 29, 18.5, 536/124; 524/785; 252/62.54, 62.51; 525/54.1, 54.4

[56] References Cited

U.S. PATENT DOCUMENTS 3,970,518 7/1976 Giaever ................................ 435/239
4,177,253 12/1979 Davies et al. ........................ 427/212

FOREIGN PATENT DOCUMENTS 1403359 8/1975 United Kingdom .

OTHER PUBLICATIONS

Chem Abstracts 80: 117706c, "Immobilization of Enzymes on Magnetic Particles", Van Leeputten et al.
B. Gutte, et al., *J. Biol. Chem.*, 246(6): 1922 (1971).
S. L. Beaucage et al., *Tet. Letters* 22(20): 1859 (1981).
Matteucci and Caruthers, *J. Am. Chem. Soc.*, 103 (11):3185–91 (1981).
Yajima and Fujii, *J. Chem. Soc.*, (Perkins Trans. I): 789–831 (1981).
Bean and Livingston, *J. Appl. Phys.*, Suppl. to vol. 30 (4):1205 (1959).
Vandenberghe et al., *J. Magnetism Mag. Materials* 15–18: 1117–18 (1980).
Matejevic, Acc. Chem. Res. 14:22–9 (1981).
R. Newbower, *IEEE Transactions on Magnetics*, MA6-9, 445 (1973).
S. Margel et al., J. Imm. Methods 28: 341–53 (1979).
A. Senyei et al, *J. App. Phys. 49(6): 3578 (1978)*.
K. Widder et al., *Proc. Soc. Exp. Bio. Med.* 58:141 (1978).
Mosbach and Schroder, *FEBS Letters* 102(1): 112 (1979).
R. Molday et al., *Nature* 268:437 (1977).
Mosbach and Anderson, *Nature* 270:259 (1977).
Zaborsky, Meth. Enzymol. 44: 324 (1976).
Maxam and Gilbert, *Proc. Nat. Acad. Sci. USA* 74:560 (1977).

*Primary Examiner*—Morton Foelak
*Assistant Examiner*—Nathan M. Nutter
*Attorney, Agent, or Firm*—Sewall P. Bronstein; Gregory Williams

[57] ABSTRACT

A support system for organic synthesis comprising magnetic particles in a dispersion medium covalently attached to functional groups having affinity for polymer subunits, and methods for making and using the support system, e.g. for synthesis of oligodeoxynucleotides and polypeptides.

28 Claims, No Drawings

MAGNETIC PARTICLES AS SUPPORTS FOR ORGANIC SYNTHESIS

This is a Continuation-in-Part of Ser. No. 449,399, filed May 31, 1983, now abandoned.

BACKGROUND OF THE INVENTION

The present invention relates to compositions, products and methods for use in synthesis of organic compounds specifically to products and methods relating to the use of magnetic particles covalently bound to reactive moieties as supports for organic synthesis.

SETTING FOR THE INVENTION

Chemical transformations requiring the interaction of two or more species, reagents or substrates, often require the separation of product from excese reagent, untransformed reactants, by-products, solvents, etc., after the reaction is completed. Such separations are costly, time consuming, and often limit the quality and purity of the product produced.

To avoid these problems, chemical transformations have been conducted in media containing two phases, with one participant in the reaction affixed to a solid phase, while the remaining components reside in solution. The solid phase is often an organic polymeric substance, hence the terms "solid-phase reactions" and "polymer supported reactions" are often used synonymously. The art of solid phase synthesis has expanded rapidly in recent years, and has been reviewed in: P. Hodge and D. C. Sherrington, editors, *Polymer-supported Reactions in Organic Synthesis*, N.Y., John Wiley and Sons, 1980, which is incorporated herein by reference.

The ease of operation of reactions and other advantages have led to the use of solid supports for executing numerous chemical transformations, e.g., in the synthesis of polypeptides on polystyrene beads, B. Gutte, et al., *J. Biol. Chem.*, 246:1922 (1971), and synthesis of DNA, RNA or polypeptides on macroporous silica gel, S. L. Beaucage et al., *Tet. Letters* 22:1859 (1981); Matteucci and Caruthers, *J. Am. Chem. Soc.* 103(11):3185-91 (1981), which are incorporated herein by reference. However, previous methods of chemical transformation that employ reageents or substrates on solid supports suffer from some serious disadvantages.

Because of the porous nature of the supports conventionally used for synthesis of DNA, RNA, polypeptides, polymers or other oligomers, for example, most of the growing oligomers are attached to walls on the inside of the solid support. This gives rise to a problem of accessibility between the growing oligomer and the reagent. Large reagents are not accessible to the growing nucleic acid, and are generally excluded altogether. Other reagents for elongation and chemical transformation must diffuse slowly through the support to react with the supported substrate.

Thus, molecules in solution entering into chemical reaction with molecules affixed to the support must diffuse through the pores to react. These disadvantages lead to slow reaction rates, often not the same for all supported molecules, incomplete reactions, and poor yields, especially when the diffusing molecule is large. Further, different classes of sites (e.g. within or without the pores) have displayed different kinetic behavior and synthetic failure.

The absence of uniform reagent accessibility has also adversely affected attempts at oligomer synthesis via automation, and other problems have occurred as well. For example, automation has proven difficult to apply to chemical synthesis because channels form in the beds of conventional solid supports through which reagents must pass. This channeling effect is not conducive to the formation of homogeneous product. The heterogenities which result lead to synthetic oligomers which are difficult to purify—the desired oligomer (if produced) is hard to separate from contaminating oligomers which do not have the desired structure.

A synthesis totally in solution is preferable and provides cleaner products and higher net yields. See H. Yajima and N. Fujii, *J. Chem. Soc.* (Perkins Trans I):7-89-831 (1981), which is incorporated herein by reference. However, synthesis in solution requires the tedious isolation of each synthetic intermediate product.

It has now been found that non-porous magnetic particles can provide excellent supports for synthesis of organic compounds, especially for oligomers such as DNA, RNA, polypeptides, polymers and other multiunit molecules having defined sequences, by attaching a growing oligomer chain to a small magnetic particle. These supports permit chemical transformations having all of the advantages of previous solid supports listed above, yet none of the disadvantages of such supports.

Reaction work-up is simplified because the supported species are easily separated from the non-supported species by magnetic removal. In some cases, this makes it possible to avoid exposing the reaction product(s) to water or to avoid a chromatographic separation in the reaction. If an excess of a reagent results in a greater reaction yield, then the excess can be used without causing separation problems. When a magnetic particle-supported reagent is used, the spent reagent is easily recovered and can possibly be recycled. This is very important economically, and can make it worthwhile to prepare complex supported reagents. Since, in most cases, magnetic separation and washing of the oligomer are all that is required to work up the reaction product at any particular stage, it becomes feasible to automate the process. As magnetic particles are insoluble and non-volatile, they are non-toxic and odorless. Hence, carrying out reactions involving toxic and odiferous compounds affixed to the solid support may be more acceptable environmentally than the ccrresponding reactions in solution.

As the separation of magnetic particle-supported products from excess reagents and by-products is uncomplicated and easily accomplished, it is possible to perform a sequence of reactions repetitively on a single substrate bound to a solid support. This is valuable for synthesizing oligomeric substances such as DNA, RNA, and polypeptides with defined sequences of nucleic acids or amino acids, by repetitively adding a single nucleotide or amino acid to a growing chain of such monomer units covalently affixed to the solid support.

Preferably the magnetic support particles are single domain magnets, exist as colloidal suspension in the reaction mixture, and are "superparamagnetic" exhibiting no residual ferromagnetism. C. P. Bean and T. D. Livingston, *J. Appl. Phys.*, Suppl. to Vol. 30:120 (1959), the disclosure of which is incorporated herein by reference. Preferably the particles are magnetite particles, although they can also be other magnetic metal or metal oxides, whether in pure, alloy or composite form, so long as they have a reactive surface. Other materials that may be used individually or in combination with iron, include but are not limited to cobalt, nickel, silicon etc. Methods of making magnetite or metal or metal oxide particles are disclosed in Vandenberghe et al., "Preparation and Magnetic Properties of Ultra-Fine Cobalt Ferrites," *J. of Magnetism and Magnetic Materials* 15–18:1117–18 (1980); E. Matijevic, "Monodispersed Metal (Hydrous) Oxides - A Fascinating Field of Colloidal Science" *Acc. Chem. Res.* 14:22–29 (1981), the disclosures of which are incorporated herein by reference.

Previous utilization of magnetic particles has included: magnetic fluids in the blood, R. Newbower, *IEEE Transactions On Magnetics* MAG-9, 445 (1973); attachment of functional groups for separation of biomolecules, U.S Pat. Nos. 3,970,518 to I. Giaever; labeling of cell-surface receptors, S. Margel et al., *J. Imm. Meth.* 28:341-53 (1979); attachment to drugs for magnetic targeting during therapeutics, A. Senyei et al., *J. App. Phys.*, 49(6):3578 (1978), K. Widder et al., *Pro. Soc. Exp. Bio. Med.*, 58:141 (1978), K. Mosbach and U. Schroeder, *FEBS Letters* 102:112 (1979); selective separation of viruses, bacteria and other cells. R. Molday et al., *Nature* 268:437 (1977); and incorporation of magnetic particles as support in gel affinity chromatography for biological polymers, K. Mosbach and L. Anderson, *Nature* 270:359 (1977), which are incorporated herein by reference. However, such have not previously been used as supports for chemical synthesis.

The particles in accordance with the invention have a specific functionality covalently bound to their surface by a coupling agent. The magnetite particles are derivatized by a silylation, permitting selective support of desired functional groups. Growing oligomers may then be linked to the appropriate functional groups, permitting the synthesis of DNA, RNA, polypeptides or other oligomers using the same chemistry for oligomer elongation that is used on classical solid supports. Preferably, the remaining reactive groups on the surface of the magnetic particles are blocked from further reaction, e.g. with non-reactive silane, prior to carrying out the oligomer synthesis.

The preferred magnetic particles are non-porous, which permits all attached reagents and substrates to be affixed to the surface of the particle. Blocking reactive sites on the particular surface which are not reacted with the coupling agent prevents unwanted side reactions. Furthermore, such derivatized magnetic particles preferably exist as colloidal suspensions. As such, reagents and substrates affixed to the surface of the particle extend directly into the solution surrounding the particle. They react with dissolved reagents and substrates in solution with rates and yields characteristic of reactions in solution, rather than rates associated with previous solid supported reactions.

Colloidal suspensions of the magnetic particles are difficult or impossible to remove from solvent by filtration. However, they are readily separated from solution by application of a magnetic field.

Additional advantages accrue if the particles are small, preferably less than 100,000 Angstroms. With decreasing size, the ratio of surface area to volume of the particles increases, permitting more functional groups to be attached per unit weight of magnetic particles. Furthermore, the smaller the particle, the better it stays in colloidal suspension. Finally, additional advantages accrue if the diameter of the magnetic particles is less than approximately 10,000 Angstroms. Preferably, the magnetic particles are single domain magnets, which display superparamagnetism, resulting in stronger attraction in external gradients of magnetic fields, and an absence of residual ferromagnetism after the external field is removed.

The magnetic particles can be used as solid supports in the same capacities as those now occupied by previous solid supports. This includes attaching small molecules to the support that are able to undergo chemical transformation and easy recovery, or alternatively, attaching reagents to the solid support, permitting the easy separation of the product in solution and/or the recovery and recycling of the reagent.

The coupling or linking agent must be able to attach to the particle and must be readily reactable with the desired oligomer subunit, or with other linker subunits which can be readily reacted with the desired oligomer subunit to form an appropriate support therefore. In that way, one end of the coupling agent is covalently bound to the particulate colloid, in suspension, and the oligomer subunit, in turn, is bound, preferably covalently, to the other end of the coupling agent. Further oligomer subunits are brought in contact with the oligomer subunit attached to the support ("initial oligomer subunit") so that a series of oligomer subunits can react with each other sequentially, thus forming an oligomer which is bound to the initial oligomer subunit.

The preferred bonding or linking agents in accordance with the present invention possess appropriate reactivity at each end of the molecule, for the magnetic support molecules and the initial oligomer subunit, respectively. The preferred coupling agents for use with this invention are silane linking agents, which comprise a silicon portion, which has reactivity with oxygen or hydroxyl groups on the metal particle surface, and an organic portion, which provides an easily reactable functional group, e.g., amino, carboxyl, hydroxyl, etc., so that oligomer subunits can be readily attached at that end of the molecule. The inorganic reactive end of the molecule is tailored to the metal, metal oxide or other inorganic material which will serve as the synthesis support. The organic functional end of the bonding or coupling agent should be structured to react with a subunit or precursor of the specific oligomer to be synthesized. A number of preferred types of organosilane linking agents are disclosed in *Silicon Compounds, Register and Review*, published by Petrarch Systems, Bristol, Pa., (1982), e.g. trialkylsilylchlorides and dialkylsilyldichlorides, the disclosure of which is incorporated herein by reference.

This invention provides all of the advantages of previous solid supports for oligomer synthesis without the accompanying disadvantages. Deoxyribonucleic acid oligomers ten bases long have been routinely prepared in greater than 95% yield for each coupling step using magnetic solid supports. This contrasts markedly with similar synthesis on silica supports, e.g. silica gel, where yields are erratic and occasionally as low as 10% for a single coupling step.

While not wishing to be bound by theory, it is believed that the superior results achieved with the present invention may arise, at least in part, from the fact that the sites of attachment of the growing oligomer are distributed on the surface of the particle, which itself is in a colloidal suspension, and thus are uniformly available to successive reagents dissolved in solution. With the preferred non-porous particles, functional groups are not contained in restrictive pores, and reagents need not diffuse through pores to reach the sites for reaction. Since the particles are in suspension, not in a bed, channeling does not occur as a result of successive reagent treatments. The improved separability of the supported oligomer synthesis sites may also contribute to the improved results.

It is an object of the present invention to provide a solid support for the chemical transformation of reactive molecules affixed to that support, which displays all of the advantages of classical solid supports but none of the disadvantages. Another object of the present invention is to provide a solid support system for the chemical transformation of reactive molecules affixed to a support uniformly available to reagents in solution and readily separable from those reagents. It is also an object to provide a non-porous particle to which functional groups may be attached and still not be confined to restrictive pores. It is also an object of this invention to provide a particle effectively in solution to which functional groups may be attached as precursors for a molecular elongation process. It is also an object of the present invention to provide a method of polymer synthesis adaptable to automation producing a relatively high yield. It is also an object to provide a process for separation of synthesized oligomers from a support system utilizing magnetic particles.

It is also an object of this invention to provide a method for the synthesis of oligomers such as DNA, RNA, and polypeptides that is adaptable to automation producing relatively high yields.

SUMMARY OF THE INVENTION

The invention herein comprises compositions, products and methods for an in vitro support system for synthesis of organic oligomers, and separation of the oligomers from the reactants. Magnetic non-porous particles of small dimension (preferably 10–1000,000 Angstroms) are covalently bound to functional groups, such as amino, carboxyl, hydroxyl, etc., via silylation. Remaining nucleophilic sites are preferably blocked by silylation. A growing polymer chain is then attached to the functional group. The particles preferably exist as a colloidal suspension in a dispersion medium. The magnetic particle acts as a solid support system for synthesis of high molecular weight substances and the colloidal suspension allows the reaction to occur as effectively as if the reactants were in solution. The product may be isolated and subsequently removed by activation of a magnetic field to collect the support system.

DETAILED DESCRIPTION OF THE INVENTION

In accordance with the present invention, small particles of magnetic metal or metal oxide are attached to an organosilane coupling agent, which in turn is attachable to an oligomer subunit so that oligomer subunits can be attached to the support system and used for oligomer synthesis. For example, magnetite [$Fe_3O_4$] particles can be prepared by pyrolysis of ferrous formate particles in a stream of dry argon at 350° C. The particles of ferrous formate may be prepared by drying an aerosol of a ferrous formate solution in a stream of heated air at 180°–220° C. The average size of the magnetite particles can be controlled by varying the concentration of the ferrous formate solution, by varying the size of the aerosol droplets, or by milling, as will be appreciated by those skilled in that art.

These magnetic particles may preferably then be coated with silica, e.g. by reaction with solutions of sodium silicate in water or in mixtures of ethanol and water.

The compositions of the present invention are made by derivatizing the support particle by silylation. Silylation is the replacement of an active hydrogen of a protic material with a substitute silicon atom. Preferably, the derivatized support particle is then brought in contact with reagents containing oligomer subunits under reaction conditions which will vary depending upon the type of oligomer being constructed and the functional group of the coupling agent.

The preferred coupling agents for use in the present invention are organosilanes of the general formula:

$$Si(X)_n[R_m(Y)_p]_{4-n} \quad (1)$$

where Si is the silicon of the organosilane coupling or linking agent, X is a leaving group i.e., an organic moiety which can be displaced by the bonds formed between silicon and the reactive groups on the support surface. X may be alkoxy, preferably lower alkoxy, alkenyloxy, alkaryloxy, aryloxy, alkynyloxy, halo or amino, preferably a secondary amino e.g., dialkylamino. R is a linking group—a bond or an organic moiety which can link the silicon, or another linking group attached directly or indirectly to the silicon, to a functional group which can serve as the point of attachment of the oligomer subunit which is to be bound to the substrate, e.g., the initial subunit of the oligomer which is to be synthesized. Because it is a linker, R must be at least bifunctional, but R may also be tri- or tetrafunctional. Thus, any given R group may be bound to up to three functional groups or further linking groups, in addition to the moiety through which it is directly or indirectly attached to the silicon. Typically, R will be alkylene, e.g., methylene or polymethylene, and where it is desired to space the functional group(s) which will ultimately take part in the synthesis reaction in a position which is removed from the metallic support, R may be long chain alkylene, e.g., preferably a long chain polymethylene. However, R may generally by any multifunctional derivative of alkyl, alkylene, alkenyl, alkynyl, aryl, alkaryl or aralkyl groups, and can include ester, amino, amido, ether, thioether or other linking functional groups where the group consists preferably or more than five atoms in length and more preferably fifteen atoms or more. Y is simply a functional group which can react with and bind the reactant to its desired support, e.g., an oligomer subunit, to bind that reactant, through the linking groups and silicon bonds, to the synthesis support particle. The nature of the functional group depends on the nature of the reactant, (e.g. initial oligomer subunit) to which it is to bind. Preferably, Y is an amino, hydroxyl, carboxyl or other functional group which will covalently attach to a linker group and which will covalently combine with the reactant it is desired to support (e.g. an oligomer subunit). "n" is an integer having a value of 1–3, reflecting the fact that the silicon can be attached to up to three leaving groups, in addition to the linker chain for the initial oligomer subunit. At least one of those leaving groups must be replaced with a bond between the silicon and the particle surface, and up to three may be so replaced. "m" is an integer having a value of at least 1, which simply reflects the fact that there must be at least one linker to bind the initial oligomer subunit to the silicon portion of the coupling agent. Typically, one linker, R, e.g., a polymethylene unit of one to twenty carbons, will be used to support one functional group Y. However, more than one functional group can be attached to the organic portion of the coupling agent, either within the linker chain (e.g. Si—R—Y—R—) or branched from it,

Preferably, m is 1–3; most preferably m is 1, having a value of at least 1. This means that there must be at least one group attached to the silicon portion of the coupling agent with which the initial oligomer subunit will bind. Preferably, p has a value of 1–3, most preferably 1. If there is more one, X,Y or R group, each such group can be different from the others. Many organosilane compounds of formula (1) are commercially available, see e.g. Petrarch Systems, Inc., *Silicon Compounds*, supra.

In the particularly preferred coupling agents, X is lower alkoxy or chloro, R is an alkylene group containing at least one amido functionality, preferably having a straight chain of at least five and preferably fifteen or more atoms, and Y is an amino, hydroxyl or carboxyl group. Such coupling agents include:

N-2-aminoethyl-3-aminopropyltrimethoxysilane
Chloromethylphenyltrimethoxysilane
N,N-dimethylaminopropyltrimethoxysilane
4[2-(trichlorosilyl)ethyl]pyridine
3-Bromopropyltrimethoxysilane, and
1-Trimethoxysilyl-2-(p-m-aminomethyl)-phenylethane, and the like.

Linkages between the coupling agent and the surface of the magnetic particle can be stabilized by covalently crosslinking some of the functional groups (Y) of the coupling agent having the general formula (1) to functional groups (Y) of other molecules of the same coupling agent or of other coupling agents having the general formula (1). Some covalent crosslinks can be chemically synthesized after the coupling agents are affixed to the surface of the magnetic particle either by direct linking between Y groups or by using bifunctional or polyfunctional crosslinking agents corresponding to the general formula:

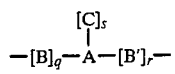 (1a)

wherein B and B' are chemical bonds or functional groups which react to form covalent bonds with the functional group Y of the coupling agent and a linking group designated as A in equation 1a. Linking group A is a chemical bond or functional group which bridges between the Y groups through the moieties B and B'. A may serve as the support for chemical synthesis, e.g. of amino acids or DNA or other oligomers by attachment of one of the elements of the oligomer (e.g. an amino acid for polypeptide synthesis or a nucleotide for DNA or DNA synthesis) to the A linking agent, either directly or through a reactive group designated as C in equation (1a).

The letters q, r and s in equation 1(a) represent integers, with q and r each preferably being at least 1, and more preferably q and r amount to 3 and 7. Where A contains a group which can form a direct attachment to the oligomer subunit of interest, s can be 0. Otherwise, the attachment can be formed via a reactive group(s) where s is 1, or greater. Preferably from s is 0 to 2, and q and r is from 2 to 5.

Linking group A can be a chemical bond or any multifunctional derivative of alkyl, alklene, alkenyl, alkynyl and alkaryl, or aralkyl groups, and can have functionalities which include one or more of amino, amido, ether, thioether and others known in the art. Preferably A is a lower alkyl group, or a lower alkyl group containing an aryl, amino, amido, ether, ester, etc., functionality with lower alkyl meaning from one to about 4 carbon atoms.

B and B' may be lower alkyl, amino, carboxyl, hydroxyl, haloalkyl or other functional groups which react with the groups Y in formula (1). B and B¹ may be the same or may be different. C may be a carboxyl, ester, amino, hydroxyl or other functional group which can form a bond or attachment with the oligomer subunit or other functional group which can form a bond or attachment with the oligomer subunit or other compound or chain to be supported by the magnetic particles and synthesized or otherwise reacted.

Examples of crosslinking agents of formula (1a) includes the following:

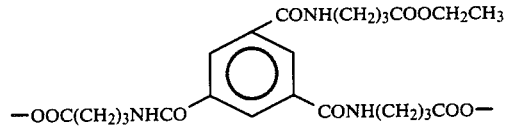

This is a trifunctional crosslinking agent in which the following elements can be considered in connection with formula (1a):

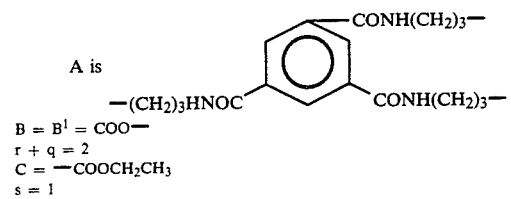

B = B¹ = COO—
r + q = 2
C = —COOCH₂CH₃
s = 1

In that compound, the oligomer subunit would be bound to the unused carboxylic acid by de-esterification.

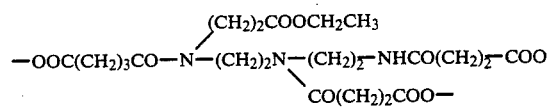

This is a trifunctional crosslinking agent in which
A = —N(CH₂)₂NH
B = B¹—CO(CH₂)₂COO—
C = (CH₂)₃ COOCH₂CH₃
q + r = 3, and
s = 1

In this compound, the oligomer subunit could be bound to the C moiety at the carboxylate group by replacement of the ethyl ester group.

—OOC(CH$_2$)$_2$CO—NH(CH$_2$)$_2$—N—(CH$_2$)$_2$NH(CH$_2$)$_2$N—(CH$_2$)$_2$NHCO(CH$_2$)COO
                               /                               \\
—OOC(CH$_2$)CO        —OOC(CH$_2$)$_2$CO

This is a tetrafunctional crosslinking agent, in which:
A=—NH(CH$_2$)$_2$—NH(CH$_2$)$_2$—N—(CH$_2$)$_2$NH—
B=B$_1$=—CO—(CH$_2$)$_2$—COO—
q+R=4
s=0

In this embodiment, the oligomer subunit to be worked on would be bound to the secondary amine of the linking group A e.g. by reacting a carboxylic acid derivative of the oligmer subunit with the amine in the presence of a condensing agent, such as dicyclohexyl carbodiimide (DCC).

The crosslinking agents of the present invention can be prepared from available starting materials and methods well known in the art. For example, the first exemplary cross linker may be prepared by condensed benzene 1,3,5-tricarboxylic acid with the ethyl ester of 4-amino butyric acid in the presence of DCC, followed by limited hydrolysis. The second compound may be prepared by reacting ethyl [2-aminoethylene-2-aminoethylene-3-amino-butyrate] with succinic anhydride. The third crosslinker can be prepared by reacting tetraethylene pentaamine with four molar equivalents of succinic anhydride.

Alternatively, coupling agents may be covalently linked before they are attached to the surface of the magnetic particle using crosslinking agents having the general formula (1a). Also, several organosilane compounds are commercially available that contain two reactive silicon coupling agents of the general formula (1) connected by crosslinking group, see e.g. Petrarch Systems, Inc., Silicon Compounds, supra.

Coupling agents of this type include:
bis[3-(trimethoxysilyl)-propyl]ethylenediamine.
bis[3-(triethoxysilyl)propyl]amine
bis[3-(triethoxysilyl)propyl]tetrasulfide The most preferable coupling agents are ones obtained by reacting aminopropyltriethoxysilane and bis[3-(trimethoxysilyl)-propyl]ethylenediamine.

Using various silyl groups, particles may be produced having amino, carboxyl, hydroxyl or other functional groups covalently attached to the surface of the particle. Procedures for the derivatization of metal oxides generally may be employed. For example, reaction of magnetite particles suspended in dry toluene with coupling agents in accordance with formula (1) in which at least one Y is amino, such as aminopropyltriethoxysilane, yields particles covalently linked to an amino functionality. See O. R. Zaborsky, *Meth. Enzymol.*, 44:317 (1976), which is incorporated herein by reference. It is preferred to avoid the use of solvents during silylation which may react with the organic end of the linking agents, such as amines or alkylthiols. The amino functionality can then be directly covalently attached to reagents or substrates to participate in a chemical transformation, or longer spacer arms can be attached which, in turn, are covalently attached to the desired reagent or substrate. For example, the amino functionality can be succinylated with succinic anhydride and reacted with an appropriately protected nucleoside in the usual manner for synthesis of DNA oligomers. See *J. Am. Chem. Soc.*, 103, supra. Other reactions may require some rigorous conditions as will be appreciated by those skilled in the art.

As noted above, it is preferred that the magnetic particles be coated with silicon, e.g. from an aqueous sodium silicate solution, prior to derivatization with the silyl group of choice. This results in a higher binding of the silyl groups being covalently attached to the particle surface. Without wishing to be bound by theory, it is believed that this occurs because this coating presents more of an opportunity for coupling agents to be bound and/or because the silicon oxide coating forms a strong intermediate bond to the ion in the particle, possibly by chemical reaction to form ion silicates, and/or the incomplete particles may be to some extent physically entrapped in a silicone oxide gel, to which the coupling of agents can be bound. The silicon coating is preferably formed in aqueous medium, e.g. by exposure of the particles to an aqueous silicate solution followed by dehydration e.g. using non-aqueous solvents and/or heating, preferably in an inert atmosphere.

After the coupling agent has been attached to the magnetic particles, the remaining reactive groups on the particle surface are preferably blocked with blocking agents to prevent competition or interfering reactions. Known blocking agents can be used which are reactive with nucleophilic groups on the particle surface. Preferred are blocking agents having the formula:

$$Si(X)_n(R)_{4-n} \qquad (2)$$

where X is a leaving group, e.g., an alkoxy, halogen, amine, etc., preferably chloro; R is a group which is not a leaving group and which lacks any functionality which would compete or interfere with the reactions needed to adjust the coupling agent, attach the initial oligomer subunit thereto, or carry on the oligomer synthesis, such as alkyl, aryl, etc., and n is an integer having a value of 1 or 2. The R's can be the same or can be different. In the preferred case, X is chlorine, n is 1 and R is alkyl, preferably methyl.

During the blocking of unreacted sites on the particle surface, any Y's should be either (a) unreactive with the blocking reagent and/or (b) protected so as to be made unreactive with the blocking agent. In the preferred case, the unprotected functional group is carboxyl, which does not react significantly with trimethylsilylchloride.

When remaining reactive groups on the surface are blocked, e.g., trimethylsilylated, the particles are remarkably resistant to oxidation, reduction and acidic dissolution. Thus, the particles withstand 6N HCl, 0.2 M iodine in water-tetrahydrofuran mixtures, and 1 M nitric acid for an extended period of time. The surface derivatization withstands all of the conditions required for chemical synthesis of DNA, RNA and peptides, including organic solvents (acetone, benzene, dimethylsulfoxide, nitromethane, tetrahydrofuran, ether, hexane, acetonitrile, methylene chloride, chloroform, etc.), acids (zinc bromide, trichloroacetic acid, etc.), bases (pyridine, lutidine, 2 N NaOH, etc.), oxidants (iodine, nitric acid, etc.) and reductants (phosphites, sodium borohydride, etc.). The particles do appear to react with thiophenoxide. Thiophenoxide is a reagent often used to remove methyl groups from methylphosphate esters which are intermediates of in vitro nucleic acid synthesis. See Example 1. Nucleic acid synthesized on magnetic oxide supports is most preferably removed with ammonium hydroxide from the support prior to demethylation with thiophenoxide.

Thus the support particle/linking agent oligomer subunit system of the present invention generally has the structure indicated in formula 2a or 2b below:

$$M-O-Si(X)_n[R_m(Y)_p]_{3-n}-Z_w \tag{2a}$$

wherein M is the support particle with the remaining nucleophilic sites blocked; O is the oxygen of the metal oxide or hydroxide, which is bound to the silicon; Si is the silicon of the organosilane linking or coupling agent; X may be as above-defined or may be replaced by additional covalent bonding to the surface of the support particle; n is an integer having a value of 0, 1 or 2. R is as above defined; Y is as above defined; m is as above defined; p is as aboved defined.

Alternatively, if crosslinking agents are used, some of the functional groups Y of the support particle/linking agent oligomer subunit system of formula (3) are crosslinked to other Y groups on the magnetic particle, in accordance with Formula (2b):

$$\begin{array}{c} M-O-Si(X)_n[R_m(Y)_p]_{3-n}[B]_q \\ \diagdown \\ \phantom{M-O-Si(X)_n[R_m(Y)_p]_{3-n}[B]_}A-[C]_sZ_n \\ \diagup \\ M-O-Si(X)_n[R_m(Y)_p]_{3-n}[B']_r \end{array} \tag{2b}$$

wherein M is the support particle, O is the oxygen of the metal oxide or hydroxide, Si is silicon, X is a leaving group, R is a linking group, Y is a functional group which can react with and bind the oligomer subunit or a group linked thereto, or cross linking agents B and B' which are chemical bonds or functional groups which react to form covalent bonds with the functional group Y, A is a linking group wich bridges the Y groups and is bound to the oligomer subunit to be worked on, either directly or through reactive group C, n is an integer having a value of 1 to 3, m is an integer having a value of at least 1, p is an integer having a value of 1–3, q and r are integers having the value of at least 1, q+r preferably being from 3–7, and s is 0 to 5.

M in either formula is any magnetic particle, having reactive groups on its surface, which can form bonds with silicon. Preferably, the magnetic particles are less than 1 millimeter in average diameter, since the smaller the particle, the greater the surface area, and the more available the reactive groups attached to the surface will be. More preferably, the particles are of a size which permits them to be contained in the reaction mixture in a colloidal suspension, e.g., below about 100,00 Angstroms. Most preferably, the particles are much smaller, e.g., between about 10 and 10,000 Angstroms, and are single magnetic domain particles, which do not exhibit residual magnetism when extracted from a magnetic field. Such single domain particles are "superparamagnetic," as dicussed above. Such particles exhibit greater magnetic force in a given magnetic field per unit volume or per unit mass, than multidomain particles.

The preferred material for component M is magnetite, although it can be other magnetic metals or metal oxides, whether in pure, alloy or composite form, so long as they have the required paramagnetism and reactive surfaces. Other materials that can be used in place of or in combination with iron include but are not limited to silicon, cobalt, nickel and other elements of Group VIII of the periodic table of the elements. Such particles can be made by the methods disclosed in this application or by the methods discussed by Vandenberghe et al., or Matijevic, discussed supra, or may be purchased commercially from various sources, including Ferrofluidics Inc., of Nashua, N.H., or the Bioclinical Group of Cambridge, Mass.

In one embodiment, in accordance with formula (2a), M is magnetite, $X_n$ is $(C_2H_5O-)_n$, n is 1 to 2, R is N-trimethylene-carboxamido-dimethylene ($CH_2-CH_2-CH_2-NHCO-CH_2CH_2$), Y is a carboxyl group, m w and p are 1, and Z is a deoxyribonucleic acid oligomer subunit attached to Y. This represents the product of silylation of magnetite with addition of a second linker arm and an initial oligomer subunit. The reactions which produce such an embodiment may be written as follows, with M representing the surface of the support particle:

$$M-OH+Si(X)_n[R_m(Y)_p]_{4-n}M-O-Si(X)_{n-1}[R_m(Y)_p]_{3-n}+(X) \tag{4}$$

wherein n is an integer of the value 3, 2 or 1. In this reaction, at least one of the leaving groups (X) is replaced by the silicon oxygen bond.

$$pZ+M-O-Si(X)_{n-1}[R_m(Y)_p]_3-_nM-O-Si(X)_{n-1}[R_m(Y)_p]_{3-n}-Z_p \tag{5}$$

Intermediate reactions may also take place, e.g. where the linking group (R) is expanded by adding another linking unit, or where one functional group (Y) is substituted for another.

Another preferred embodiment is identical with the preceding one, except that M is magnetite coated with silica prior to derivatization with the particle surface.

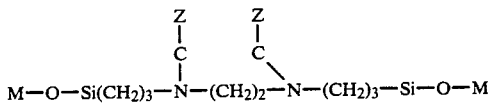

wherein O and M are as above defined; preferably M is magnetite, C is $CO(CH_2)_2CO$, and Z is a 2' deoxyribonucleotide oligomer subunit.

The method of use of appropriately derivatized particles in the present invention is direct. DNA can be synthesized in aqueous media using magnetic particles as supports. Preferably, the specific functionality covalently bound to the surface of the particle may be linked to the appropriate polymer and remain in solution pending completion of the reaction series and separation of the product. A standard repetition of a sequence of reactions, as described by S. L. Beaucage and M. A. Caruthers in *Tetrahedron Letters*, 22:1859–1862 (1981) which is incorporated herein by reference, produces oligomers of DNA attached to magnetic particles. This sequence will take approximately ten minutes per cycle and produces coupling in yields similar to the quantitative amounts mentioned above, as compared to synthesis on silica gel supports where cycle times need to be greater than one hour to obtain optimum results.

The invention will be further understood with reference to the following examples which are purely exemplary in nature and are not meant to be utilized to limit the scope of the invention.

EXAMPLE I

Derivitization of Magnetic Particles Useful in DNA Synthesis

A solution of barium formate was prepared by dissolving barium oxide powder in formic acid, the pH being adjusted to between 4 and 7 as a result. The concentration of the solution of barium formate was determined by precipitation of barium as its sulfate. This solution was then mixed with an equimolar amount of a freshly prepared solution of ferrous sulfate (0.05 M). The precipitate, barium sulfate, was removed by centrifugation. The supernatant contained a solution of ferrous formate having a concentration of approximately 0.04 M.

This solution was diluted 10:1 with deionized, deaerated water, and then immediately passed through a Niro particle generator blow drier. Inthe blow drier, the solution was atomized to form a fine aerosol, which was then dried in a stream of air between 190° and 210° C., to produce a powder of finely divided ferrous formate, presumably accompanied by small amounts of ferric formate and hydroxide. The particles were then heated for three hours at 310° C. under an inert atmosphere (argon). The heating converted the particles of ferrous formate to particles of ferrous oxide, carbon monoxide, and water in accordance with the equation:

$$2\ Fe(HCOO)_2 = 2FeO + 2CO + H_2O$$

Evolution of carbon monoxide and water was detected during the course of the heating.

Ferrous oxide is oxidized in ambient air. These particles, upon cooling, were exposed slowly to atmospheric oxygen, during which exposure they were converted to magnetite ($Fe_3O_4$) according to the following equation:

$$3\ FeO + \tfrac{1}{2}O_2 = Fe_3O_4$$

The particles were analyzed by oxidation to ferric oxide ($Fe_2O_3$), and their size was determined by electron microscopy. The particles used in this example had a median diameter of less than 500 Angstroms, and were single domain, superparamagnetic particles. However, if the particles were not of the desired size, the process could be repeated with more concentrated solutions of ferrous formate for larger particles or more dilute solutions of ferrous formate for smaller particles. The particles can also be made smaller by milling them in a high speed blender.

After the appropriate analytical procedures, the particles were derivatized. Finely divided magnetite (1 gram) was suspended in water (15 ml) with sonication. Aminopropyltriethoxysilane (1 gram) was then added to the aqueous mixture, and the pH was adjusted to 4 with 1 N HCl. The mixture was then stirred for one hour, after which the particles were recovered by application of a magnetic field. The particles were then washed and dried.

A spacer arm was than attached to the amino functionality attached to the particles. This was done by adding small portions of succinic anhydride to a stirred aqueous suspension of the particles. Several additions were made, and the pH was maintained at 7-8 throughout the addition by adding drops of 1 N NaOH. The product of the addition, magnetic particles to which were covalently appended the chain:

$$\text{SiCH}_2\text{CH}_2\text{CH}_2\text{NHCOCH}_2\text{CH}_2\text{COOH},$$
with $(OC_2H_5)_n$ above Si, was collected by application of a magnetic field, washed with water and ethanol, and dried. The value of n will vary for particular magnetite/organosilane bonds, since the organosilane can react to form 1, 2 or 3 bonds with the reactive groups of the metal particles.

The dried particles were then suspended in anhydrous toluene and treated with trimethylsilychloride. This treatment trimethylsilylated any unreacted nucleophilic sites, rendering them unreactive under conditions of subsequent synthesis as stated below. The particles were recovered with a magnetic field, washed with acetone and water, and used as supports for synthesis.

5'-O-dimethoxytritylthymidine was attached by its 3'-hydroxyl group to the carboxyl group affixed to the magnetic particle, using dicyclohexylcarbodiimide as a condensing reagent, in a procedure similar to that used by Caruthers and coworkers, *Tet. Let.*, 22, supra. Successive elongation of the DNA chain was made by successive repetition of a sequence of three organic reactions. Each of the reacting reagents was added in an appropriate solvent, and the particles dispersed in the solvent to initiate the reaction. The reactions were as follows:

1. Removal of the 5'-dimethoxytrityl blocking group, leaving a free 5'-hydroxyl group, with a solution of zinc bromide in nitromethane, carried out at room temperature, with occasional shaking. As the product of this reaction is brightly colored, the extent of the reaction could be determined spectrophotometrically.

2. Condensation of 5'-dimethoxytritylthymidine-3'-O-dimethylaminomethoxyphosphine with the free 5'-hydroxyl group of the thymidine, from Step 1 above, attached to the magnetic particle through the Y carboxyl group, done in the presence of tetrazole as acid in acetonitrile as solvent. The reaction conditions were again room temperature, with stirring.

3. Oxidation of the resulting trivalent phosphorus compound formed above was accomplished by using a solution of 0.2 M iodine in a 1:2:1 water-tetrahydrofuran-lutidine mixture, at room temperature, with stirring.

These three steps are well known in the art as steps leading to the preparation of DNA oligomers. In this example, d(T10) was prepared, removed from the magnetic support with ammonium hydroxide, demethylated with thiophenoxide, and analyzed by sequence using the method of Maxam and Gilbert, *Proc. Nat. Acad. Sci. USA* 74:560 (1977), which is incorporated herein by reference.

The reaction sequences are as follows:

MAGNETITE-OH + $(CH_3CH_2O)_3Si(CH_2)_3NH_2$
|    |
OH  pH4      Aminopropyltriethoxysilane
1 N HCl
↓

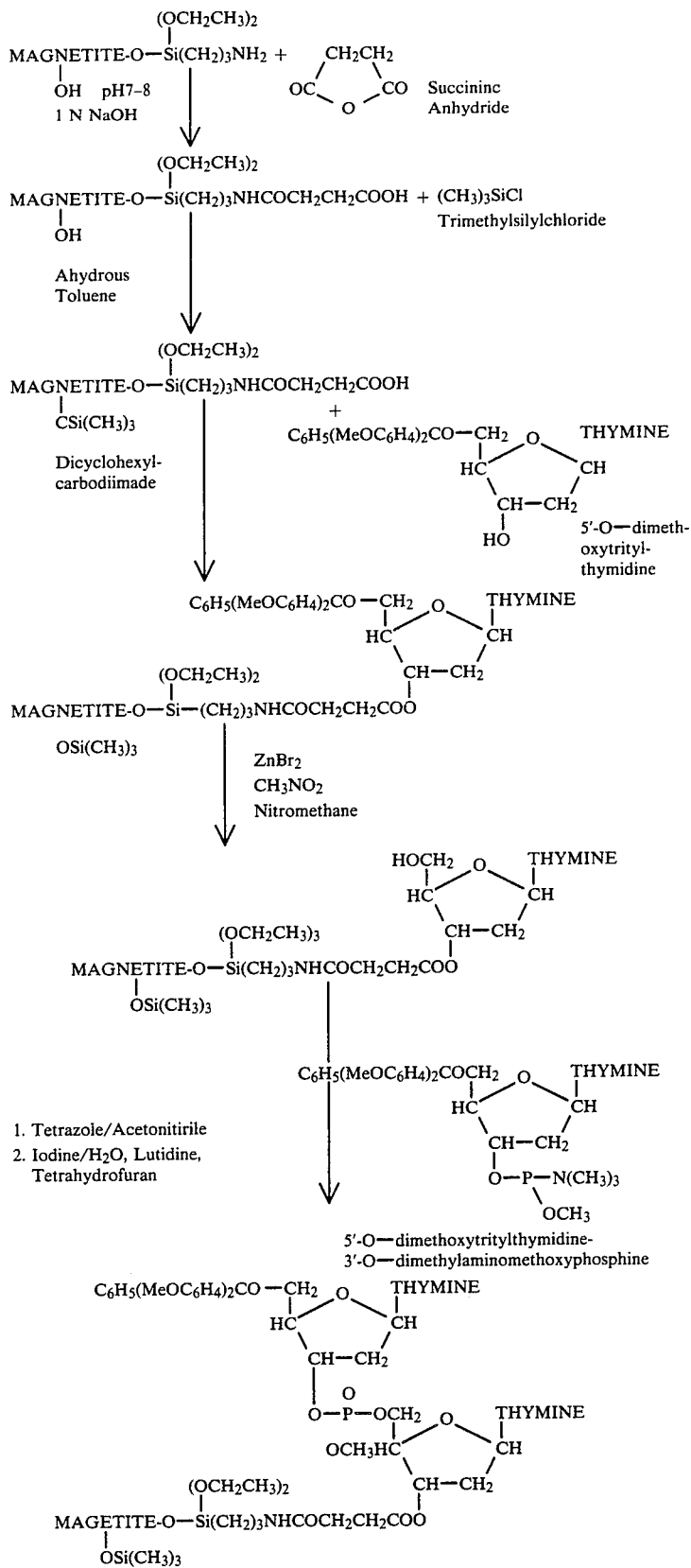
EXAMPLE 2
Use of Different Particles
In a second example, particles available commercially as Biosorb C were obtained from the Bioclinical Group Inc. of Cambridge, Mass. The dimensions of these particles, were greater than 1000 but less than 100,000 Angstroms. These particles were of unknown composition, advertised only as having carboxyl groups covalently attached to magnetite. The length and chemical nature of the spacer was unknown. The particles were not single domain, and were not superparamagnetic. Between each step, the particles were removed from suspension with a magnet, and then resuspended by demagnetization in the discharging field of a demagnetizer.

5'O-dimethoxytritylthymidine was covalently coupled to the carboxyl group appended to the magnetic particles as described in steps 1, 2 and 3 in Example 1, and an oligomer ten thymidines long was synthesized. The magnetic particles were first reacted with trimethylsilyl chloride in anhydrous toluene, as described in Example 1, so as to block any remaining nucleophilic sites on the surface of the particle. The oligomer was prepared in 70% yield based on the number of sites on the particle originally covalently bound to the monomer, the yield being judged by the extend of color released in the removal of the blocking 5'-O-dimethoxytrityl group in each cycle, as measured at 400 nm in a spectrophotometer.

EXAMPLE 3

Silicon Coating of Magnetic Particles

Finely divided magnetite (2.27 gm.), prepared by the method described in Example 1, was suspended in deionized water (30 mls), and a solution of sodium silicate (6 ml, Fischer, 40%) was added. The mixture was then sonicated (Branson sonic oscillator, microtip at power setting 3). To the resulting emulsion was added ethanol (95%, 7.3 ml), and the mixture was shaken for 15 min.

Deionized water was then added to the mixture of magnetic particles coated with silicate, and the particles were removed from suspension with a magnet, and repeatedly washed with hot water (30 ml) to remove excess sodium silicate until the washings showed no formation of precipitate with addition of cupric sulfate solution. The particulates were then washed with cold water (3×30 ml) and then twice with 1:1 mixture of ethanol and water, and then with ethanol, then toluene, and finally resuspended in 30 ml of anhydrous toluene. Excess water and ethanol was removed by azeotropic distillation with toluene.

Magnetic particles of prepared were than derivatized as described in Example 1.

EXAMPLE 4

Crosslinked Functional Group

Finely divided magnetite (2.0 gm.), prepared by the method described in Example 1, was suspended in dry toluene (25 ml) with sonication. To the suspenion was added bis[3-(trimethoxysilyl)-propyl]-ethylenediamine (2.0 ml of a 40% solution in methanol), and the mixture was heated at reflux for 3 hours. The particles were than removed from liquid by application of a magnetic field, washed with acetone and methanol, dried, and then further derivatized as described in Example 1.

Additional advantages and modifications of the invention disclosed herein will occur to those persons skilled in the art. Accordingly, the invention in its broader aspects is not limited to the specific details or illustrated example described. Therefore, all departures made from the detail are deemed to be within the scope of the invention as defined by the appended claims.

What is claimed is:

1. Oligomer synthesis support comprising a magnetic particle covalently bound to oligomer subunits, said oligomer subunits comprising subunits of deoxyribonucleic acid or ribonucleic acid.

2. The composition of claim 1, wherein said oligomer subunits comprise subunits of deoxyribonucleic acid.

3. The composition of claim 1, wherein said magnetic particles comprise magnetite.

4. The composition of claim 1, wherein said oligomer synthesis support exists as a colloidal suspension in a dispersion medium.

5. The composition of claim 1, wherein said magnetic particles are single domain.

6. The composition of claim 1, wherein the size of said magnetic particles is in the range of 10–100,000 Angstroms.

7. An organic synthesis support that comprises a magnetic particle having reactive sites covalently coupled to functional groups, the remaining reactive sites being blocked against reaction by silyl blocking groups.

8. The composition of claim 7, wherein said magnetic particles comprise magnetite.

9. The composition of claim 7, wherein said magnetic particles are non-porous.

10. The composition of claim 7, wherein said magnetic particles exist as a colloidal suspension in a dispersion medium.

11. The composition of claim 7, wherein said magnetic particles are single domain.

12. The composition of claim 7, wherein said magnetic particles are in the range of 10–100,000 Angstroms.

13. The composition of claim 7, wherein said magnetic particles are in the range of 10–100,000 Angstroms.

14. The composition of claim 7, wherein said functional groups are amino, carboxyl, or hydroxyl.

15. The composition of claim 7, wherein the reactive sites are blocked by reaction with a compound having the following structure:

$$Si(X)_n(R)_{4-n}$$

wherein Si is the silicon of an organosilane; X is a leaving group and member of the group alkoxy, halogen or amine; n is an integer having a value of 1 or 2; R is a member of a group of alkyl, alkenyl, alkynyl or aryl where the group contains at least one carbon atom and does not contain any reactive functionality.

16. The composition of claim 7, wherein said silyl blocking agent is trimethysilylchloride.

17. A cross-linked oligomer synthesis support having the following structure:

$$M\text{—}O\text{—}Si(X)_n[R_m(Y)_p]_{3-n}\text{—}Z$$

wherein M is the surface of a magnetic support particle; O is the oxygen of the metal oxide or hydroxide; Si is the silicon of the organosilane linking or coupling agent; X is a member of the group of alkenyloxy, alkaryloxy, alkynyloxy, alkoxy and halo; n is an integer with a value of 0, 1 or 2; is a linking group and member of a group of alkyl, alkenyl, alkynyl or aryl where the group contains more than one carbon atom; n is an integer with a value of 1, 2 or 3; Y is a member of the group of amino, hydroxyl or carboxyl which will covalently combine with an oligomer subunit or precursor; p is an integer with a value of at least 1; Z is an initial oligomer subunit.

18. The composition of claim 17 or 1, wherein said linking group is polymethylene.

19. The composition of claim 17 or 1, wherein said linking group is N-trimethylene-carboxamide-dimethylene.

20. The composition of claim 17 or 1, wherein said member Z is a deoxyribonucleic acid, ribonucleic acid or polypeptide subunit.

21. A method of making a support for organic synthesis that comprises reacting a magnetic particle with a silane coupling or linking agent and reacting the resulting product with an oligomer subunit.

22. The method of claim 21, wherein the silane coupling or linking agent has a silicon portion and an organic portion, the magnetic particle is convalently attached to said silicon portion and said oligomer subunit is reacted with the organic portion.

23. The method of claim 21, wherein said magnetic particles comprise magnetitie.

24. The method of claim 21, wherein said magnetic particles are non-porous.

25. The method of claim 21, wherein said silane coupling or linking agent has the formula:

where Si is the silicon of the organosilane linking or coupling agent; X is a member of the group of alkyoxy, alkenyloxy, alkynyloxy, alkaryloxy, aryloxy, and halo; R is a member of the group of alkyl, alkenyl, alkynyl, aryl, alkaryl, or aralkyl; m is an integer having a value of at least one; p is an integer with a value of at least one; Y is a functional group of the group amino, carboxyl or hydroxy, which can react with an oligomer subunit; n is an integer having a value of 1–3.

26. An oligomer support synthesis having the following structure:

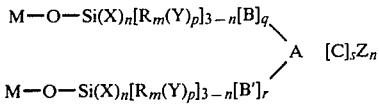

wherein M is the support particle, O is the oxygen of the metal oxide or hydroxide, Si is silicon, X is a cleaving group, R is a linking group, Y is a functional group which can react with and bind the oligomer subunit or a group linked thereto, or cross linking agents B and B' which are chemical bonds or functional groups which react to form covalent bonds with the functional group Y, A is a linking group which bridges the Y groups and is bound to the oligomer subunit to be worked on, either directly or through reactive group C, n is an integer having a value of 1 to 3, m is an integer having a value of at least 1, p is an integer having a value of 1–3, q and r are integers having the value of at least 1, q+r being from 3–7, and s is 0 to 5.

27. The support of claim 26, having the structure:

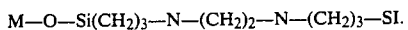

28. The support of claim 27, wherein C is $-CO(CH_2)_2 CO-$; and Z is a deoxyribonucleotide subunit.

* * * * *